United States Patent [19]

Williams

[11] Patent Number: 5,013,300
[45] Date of Patent: May 7, 1991

[54] APPARATUS FOR SUCTION LIPECTOMY SURGERY

[76] Inventor: James D. Williams, 3700 Westfall Dr., Encino, Calif. 91436

[21] Appl. No.: 321,504

[22] Filed: Mar. 9, 1989

[51] Int. Cl.⁵ .......................................... A61M 1/00
[52] U.S. Cl. .................................. 604/119; 604/283; 604/902; 433/91
[58] Field of Search ............... 604/118, 119, 280, 283, 604/317, 319, 322, 324, 326, 327, 240, 242, 243, 902, 905; 433/91, 94, 95, 96, 99, 100, 127, 128; 251/7; 403/108, 109, 378, 379; 81/177.2; 279/79

[56] References Cited

U.S. PATENT DOCUMENTS

| | | | |
|---|---|---|---|
| 2,531,730 | 11/1950 | Henderson | 604/902 |
| 3,308,825 | 3/1967 | Cruse | 604/902 |
| 3,863,635 | 2/1975 | Swatman | 433/95 |
| 3,889,682 | 6/1975 | Denis et al. | 604/119 |
| 3,964,484 | 6/1976 | Reynold et al. | 604/902 |
| 4,079,965 | 3/1978 | Moughty et al. | 403/108 |
| 4,451,257 | 10/1981 | Atchley | 604/902 |
| 4,468,217 | 8/1984 | Kuzmick et al. | 604/48 |
| 4,534,542 | 8/1985 | Russo | 604/119 |
| 4,536,180 | 8/1985 | Johnson | 604/119 |
| 4,568,332 | 2/1986 | Shippert | 604/119 |
| 4,627,834 | 12/1986 | Lee | 604/902 |
| 4,699,138 | 10/1987 | Behrstock | 604/119 |
| 4,713,053 | 12/1987 | Lee | 604/49 |
| 4,784,649 | 11/1988 | Imonti et al. | 604/119 |
| 4,822,343 | 4/1989 | Beiser | 604/243 |
| 4,857,063 | 8/1989 | Glenn | 604/317 |
| 4,878,900 | 11/1989 | Sundt | 604/902 |
| 4,925,450 | 5/1990 | Imonti et al. | 604/240 |

FOREIGN PATENT DOCUMENTS 0007602 6/1980 European Pat. Off. ............ 604/275

Primary Examiner—John D. Yasko
Assistant Examiner—Anthony Gutowski
Attorney, Agent, or Firm—Poms, Smith, Lande & Rose

[57] ABSTRACT

An apparatus for removing subcutaneous fatty tissue having a suction source connectable to a surgical instrument by means of a tube, the instrument having a cannula with a through passage, one end of the cannula having a configured end closure portion provided with a plurality of openings and a mounting sleeve at the other end of the cannula. A handle having a through bore receiving at one end the mounting sleeve and at the other the tube connecting to the suction source. The connection between the handle and the tube has a swivel connection for manipulation of the surgical instrument over a wide range of positions relative to said plurality of openings during withdrawal of the fatty tissue under suction forces applied subcutaneously through a skin surface incision.

2 Claims, 3 Drawing Sheets

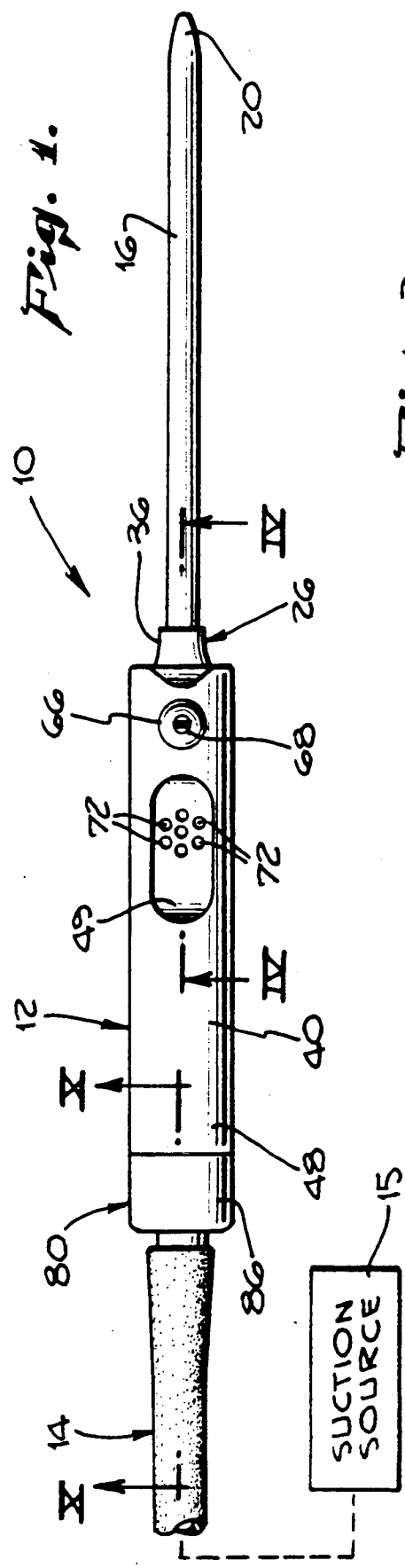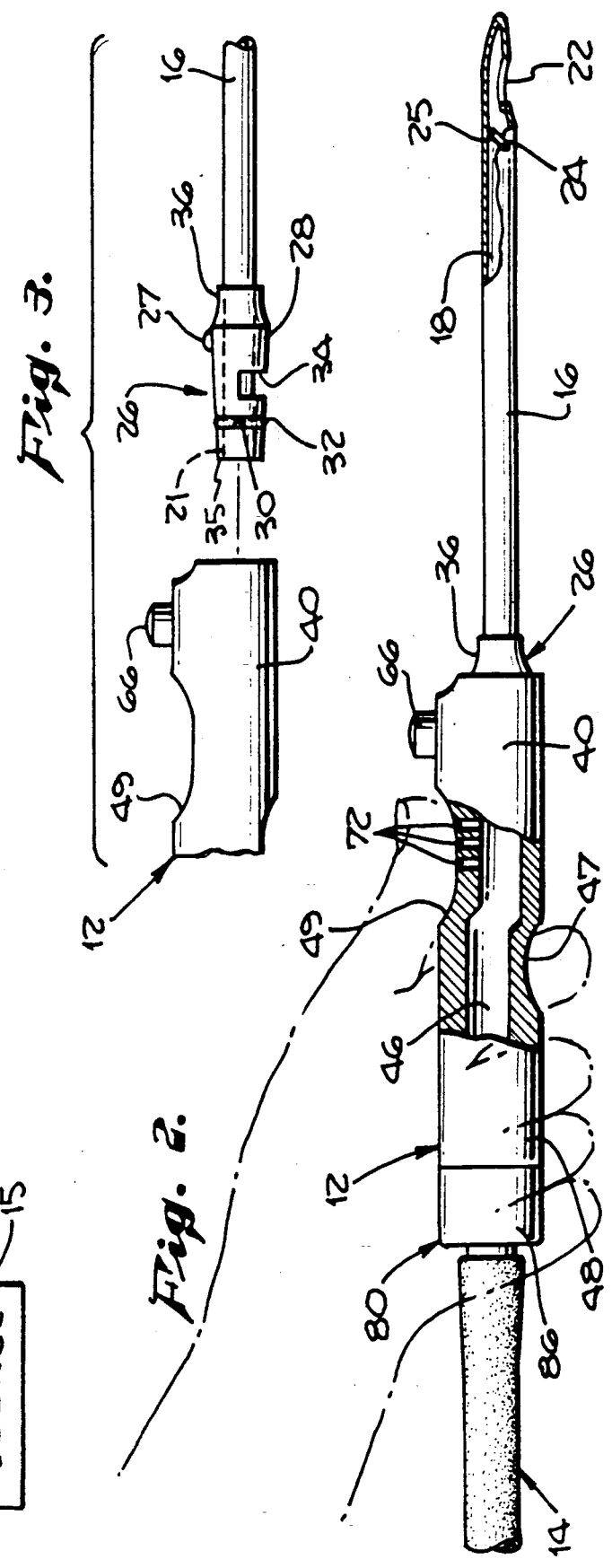

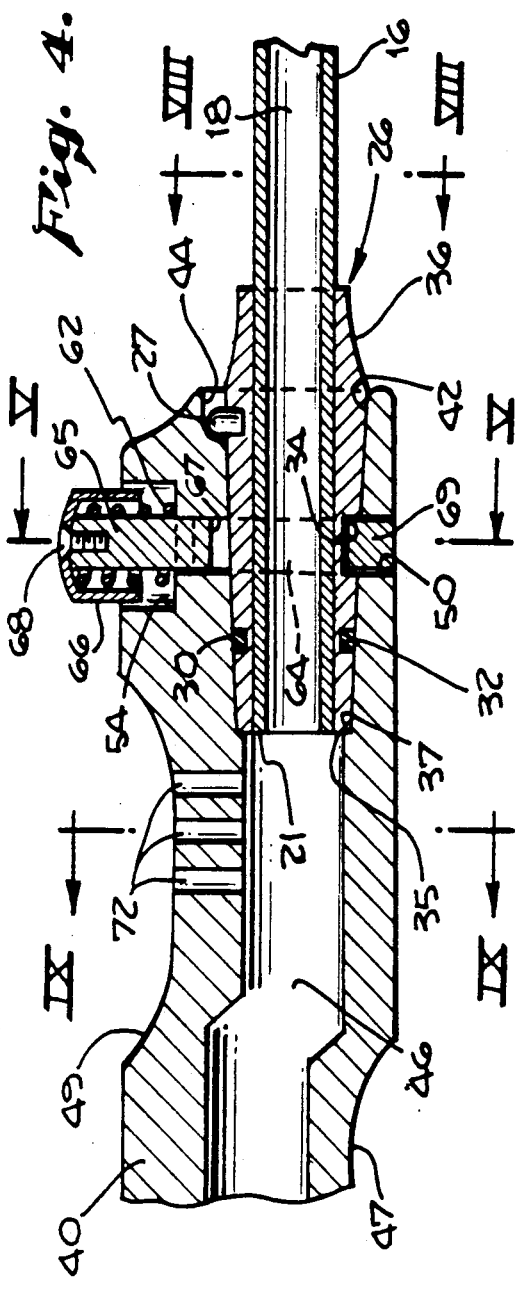

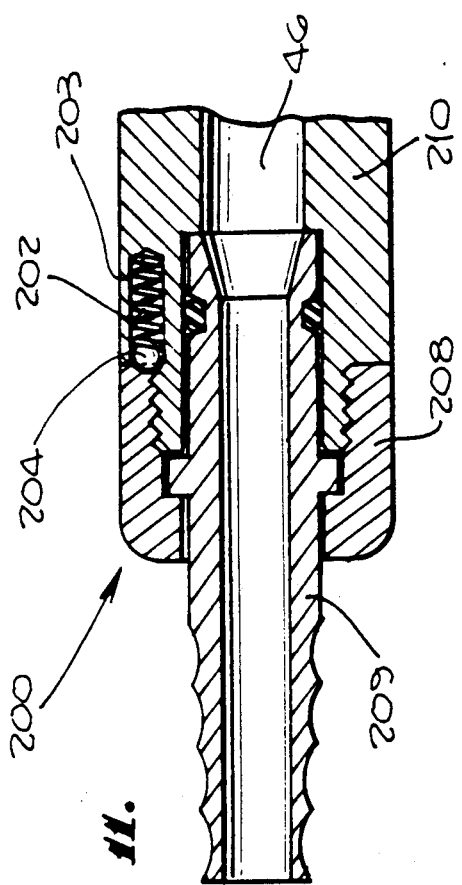
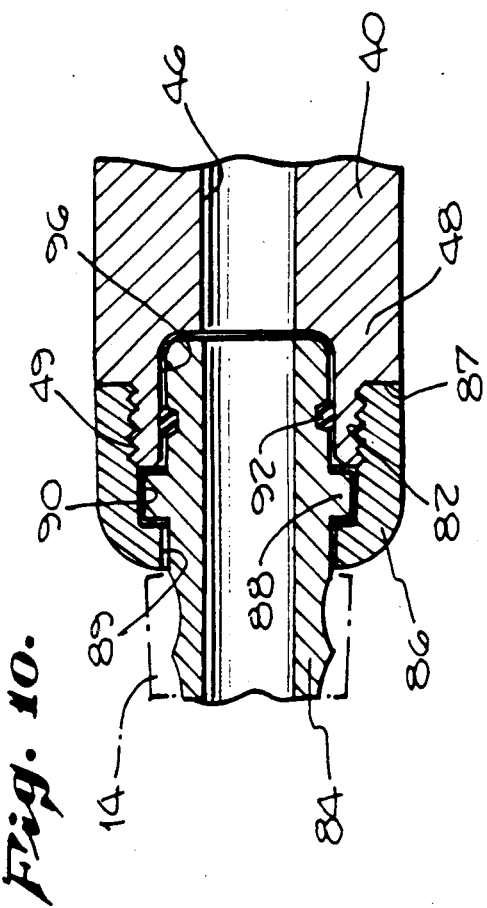
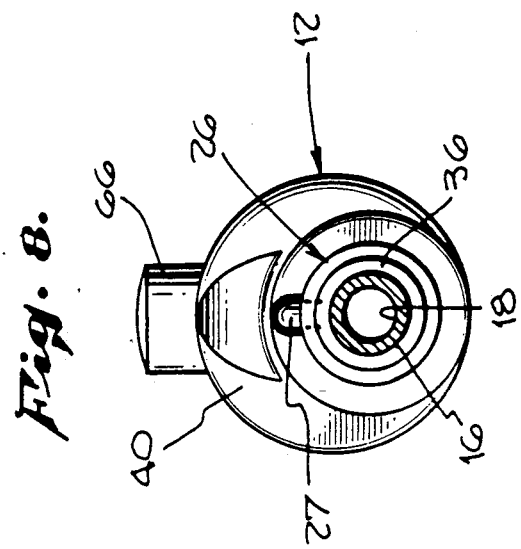
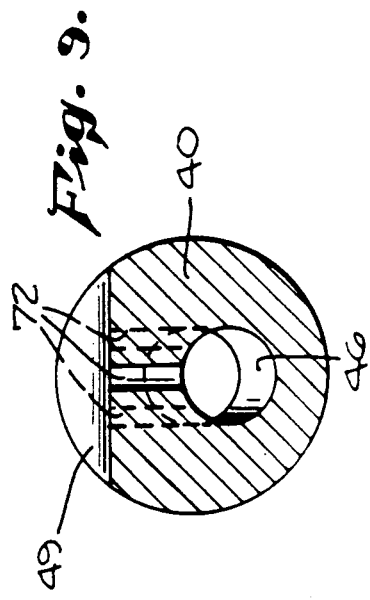

APPARATUS FOR SUCTION LIPECTOMY SURGERY

FIELD OF THE INVENTION

This invention relates to an apparatus for use in Suction Lipectomy surgery in order to remove subcutaneous fatty tissue from a human body.

BACKGROUND OF THE INVENTION

Suction lipolysis or Lipectomy is a surgical procedure for the removal of fatty tissue from selected areas of the body. The procedure consists of making a surgical incision in the skin, near the area of the body where the fatty tissue to be removed resides. The end of a cannula provided with a single or a plurality of openings is inserted into the incision and the cannula tip is directed towards the desired area under the skin. To remove the fatty tissue, a number of reciprocating strokes of the cannula are often required.

The cannula is connected to a handle with a through bore which is then connected to a suction source. The suction source is typically a vacuum pump typically of the type supplied by Wells Johnson Company, such as the Aspirator II 110 volt model 20-5010. The handle connects to the vacuum pump by a heavy gauge plastic tube. The plastic tube has to have a sufficient wall thickness not to collapse during the application of the suction force. The suction force applied aspirates the fat from the body through the cannula, handle, and the tube therethrough to a waste canister.

Depending upon the area of the body where fatty tissue is being removed, a number of differently configured cannulas are often needed. While it is possible to change the cannula, it can often be a cumbersome and slow procedure. The slowness of the procedure is undesirable because the goal with all surgery is quickness and thoroughness.

During the removal of fatty tissue the passageways in the tube, the surgical instrument, the cannula and the handle may become clogged, preventing the removal of additional fatty tissue. The surgeon must typically remove the cannula from that area of the body and out through the incision to break the vacuum and to introduce ambient air to clear the line. Such clogging of the tube or instrument is not uncommon. In clearing the line by removing the cannula and then re-inserting the cannula into the incision, the incision area is further traumatized. The incision may be subject to severe traumatization depending on the degree and extent of clogging during removal of fatty tissue. Additionally, the traumatizing of the incision as noted above can result in unattractive bruises, deforming of the incision area and other undesired results which require extended healing periods.

During removal of fatty tissue, the surgeon often needs to rotate and manipulate the instrument in order to place the cannula in a desired position. This often requires not only the full rotation of the instrument about its axis but also manipulation of the instrument through a wide range of positions. Unfortunately, the thick tube connecting the instrument to the vacuum pump often hinders and restricts such free manipulation of the instrument.

Moreover, prior proposed constructions have been designed for resolving some of the above mentioned problems. Such apparatus of this type are set forth in U.S. Pat. Nos. 3,401,690, 4,468,217, 4,536,180, 5,534,542, and 4,713,053. While some of the patented devices have claimed improvements and solutions to some of the problems noted, none solves the critical problems noted above with an apparatus or instruments addressing the need individually or as a whole.

Accordingly, principal objectives of the present invention are to provide an apparatus which enables the quick and easy changing of the cannula, solves the critical problem of clearing the line of the apparatus while inserted in the incision, or allows the desired degree of movement to properly and easily perform the surgical procedure.

SUMMARY OF INVENTION

The present invention contemplates a novel and improved apparatus for surgically removing subcutaneous tissue from the human body. The invention contemplates a surgical instrument comprising a cannula and a handle in which the cannula distal end portion is provided with opening means of novel configuration to facilitate the entry of fatty tissue into the passageway of the cannula. The cannula is mounted in the handle means in a novel manner by which the cannula may be quickly connected or disconnected from the handle providing for a quick substitution of cannulas for varying configurations. The handle includes a novel means for controlling suction forces in the through bore of the handle which communicates with the passageway int he cannula, such control feature providing convenient means for removing clogging of the passageways through which the fatty tissue is being conducted to a canister or reservoir. The invention contemplates a swivel connection between the handle means and a tissue conducting tube means which leads to the suction source and canister, the swivel means facilitating the manual manipulation of handle means through a variety and wide range of manipulation of a wide range of positions relative to the fatty tissue which is being withdrawn so that the withdrawal of fatty tissue may be effectively and readily accomplished.

Therefore, the primary object of the present invention is to provide an apparatus for removing and withdrawing fatty tissue or other biological substances in which novel features are incorporated to effectively and efficiently accomplish such a procedure or operation.

An object of the invention is to provide a novel instrument means in which openings at the distal end portion of a cannula for inflow of fatty tissue are arranged in a novel manner.

Another object of the invention is to provide a novel instrument means in which a handle means and a cannula are readily connected in a selected position for facilitating manipulation of the instrument means.

Another object of the invention is to provide a novel instrument means including a handle and a cannula in which connecting means are provided between the handle and cannula for quickly connecting and/or disconnecting the cannula from the handle means.

A still further object of the present invention is to provide a novel surgical instrument means for removal of fatty tissue by means of suction forces in which the handle means is provided with a novel control means for modifying and varying the suction forces applied to the cannula and also to the through bore of the handle and to a tube means conducting fatty tissue from the handle to a canister or receptacle receiving the removed fatty tissue.

A still further object of the invention is to provide a novel swivel means for interconnecting a handle of such a surgical instrument with a tube means conducting fatty tissue to a receptacle in which the normal restraints imposed on the handle by the tube means are minimized so that the surgical instrument may be more readily manipulated to effectively accomplish the lipectomy procedure.

A more specific object of the invention is to provide a connecting means between a handle and a cannula whereby the cannula may be quickly connected or disconnected from the handle without removal of the cannula from an incision in the skin of a patient and in which the quick connecting means positively restrains relative movement between the cannula and the handle means in an axial direction.

A still further specific object of the invention is to provide means at the connecting means between the cannula and the handle for restricting rotation of the cannula relative to the handle and for aligning the cannula with the handle relative to means for facilitating gripping of the handle in the fingers of a surgeon.

Other objects and advantages of the present invention will be readily apparent to those skilled in the art from the following description of the drawings in which an exemplary embodiment of the invention is shown.

BRIEF DESCRIPTION OF THE DRAWINGS

FIG. 1 is a top view of a surgical instrument, connecting tube and schematically shown suction source of an apparatus embodying this invention.

FIG. 2 is a side view, partly in section, of the surgical instrument and connecting tube of the apparatus.

FIG. 3 is an exploded view of a section of the surgical instrument.

FIG. 4 is an enlarged sectional view taken in the plane of FIG. 1 showing a portion of the surgical instruments in cross-section IV—IV.

FIG. 5 is a view in cross-section taken in plane V—V of FIG. 4 showing a quick disconnecting feature of the handle engaging the cannula.

FIG. 6 is a view in cross-section also taken in plane V—V of FIG. 4 showing the quick disconnecting feature of the handle disengaging the cannula.

FIG. 7 is a perspective view of the retaining ring of the quick disconnecting feature.

FIG. 8 is a cross-sectional view taken in a transverse plane indicated by line VIII—VIII of FIG. 4.

FIG. 9 is a cross-sectional view taken in a transverse plane indicated by line IX—IX of FIG. 4 showing a suction control for the surgical instrument.

FIG. 10 is a fragmentary cross-sectional view taken in a longitudinal plane indicated by line X—X of FIG. 1 showing a swivel connector.

FIG. 11 is a side view in cross-section through plane X—X of FIG. 1 showing an alternative embodiment of the swivel connector.

BRIEF DESCRIPTION OF THE PREFERRED EMBODIMENT

Referring now to the drawings, FIG. 1 illustrates apparatus 10 embodying this invention which is utilized in the surgical procedure of suction lipectomy or lipolysis for removing subcutaneous fatty tissue from localized area of the human body. Apparatus 10 includes surgical instrument means 12 and a tube means 14 which connects the surgical instrument 12 to a suction source 15 which aspirates the fatty tissue. The instrument means 12 includes a canula 16 having a distal end adapted to be inserted through an incision to at least approximately a quarter of an inch below the skins' surface and above the underlying muscle tissue. Fatty tissue present between the skin and muscle tissue is withdrawn through cannula 16, surgical means 12, and tube means 14 by suction from a vacuum suction source 15.

Cannula 16 may be of selected length and may comprise an elongated semi-rigid or semi-flexible cylindrical member of thin metal having a highly polished finished exterior surface. The preferred material to be used for cannula 16 is 304 stainless steel. Additionally, the highly polished finish on the exterior surface of the 304 stainless steel cannula 16 will result in an improved lubricity which minimizes the friction when cannula 16 is inserted into an incision and manipulated during removal of subcutaneous fatty tissue. Cannula 16 is provided with a distal end portion 20 having a configured downwardly sloping convex surface which extends below the longitudinal axis of the cannula. A cannula passageway 18 is provided with a plurality of openings at the distal end portion, one of said openings being a longitudinally extending opening 22 in the wall of the cannula end portion and spaced from the end of the cannula. Opening 22 extends longitudinally from a point approximately opposite the beginning of the downwardly sloping end portion and may terminate at an edge generally normal to the axis of the cannula. The width of longitudinal opening 22 may be less than the inner diameter of the passageway 18 of the cannula.

The plurality of openings also includes transverse openings 24, 25 (opening 25 corresponding to opening 24 on the opposite side of the cannula as viewed in FIG. 2) which are spaced from the rear edge of longitudinal opening 22 a selected distance. In this example, openings 24, 25 are inclined relative to the axis of the cannula. The lengths of openings 24 are less than the inner diameter of passageway 18 to provide sufficient metal cannula material to support the cannula distal end portion 20. It has been found that the configuration of the longitudinal opening 22 and side transverse diagonal openings 24, 25 has facilitated volume removal of fatty tissue.

As best seen in FIG. 4, the proximate end portion 21 of cannula 16 may be provided with a cannula base or mounting sleeve 26. Mounting sleeve 26 is secured to cannula end portion 21 by any suitable means such as adhesives, welding and the like. Mounting sleeve 26 may have a tapered main body portion 28 having an annular recess 30 adjacent one end for reception of a seal ring 32. Intermediate ends of the tapered body section may be provided a transverse cutout 34 for cooperation with a quick disconnect means as later described. The tapered body portion has its widest diameter spaced from the forward end of the mounting sleeve, the forward end portion 36 having an annular concave configuration. The tapered body section 28 of the mounting sleeve provides a wedge fitting into a corresponding tapered socket 42 provided in one end of handle means 40. The wedge fitting and the o-ring seal 32 provide a firm non-leaking connection between the mounting sleeve 26 and the handle means 40.

Mounting sleeve 26 is angularly positioned on the proximate end portion 21 of the cannula relative to the position of the plurality of openings 22, 24 and 25 when it is secured and fixed to the proximate end portion 21 of the cannula 16. Such positioning of mounting sleeve 26 relative to the openings at the distal end of the cannula provides a means for positioning the cannula 16 relative to the handle means 40 by use of an orienting pin 27 in the forward end of the tapered body section 28 and having an orienting pin 27 receivable within a recess 44 provided in the handle means so that the handle means and distal cannula tip are oriented in fixed relationship with respect to the handle means 40.

Handle means 40 in addition to providing a mounting for mounting sleeve 26 provides a through bore 46. At the end of handle means 40 opposite to the cannula mounting sleeve 26, bore 46 is enlarged for reception of a swivel connector means as later described at one end of tube means 14.

Handle means 40 may comprise a generally cylindrical body member adapted to be readily held and positioned in the hand of a surgeon as shown in FIG. 2 by the provision of a concave recess 47 provided in the bottom surface of the body member at approximately the mid-point and an upper thumb receiving concave recess 49 provided in the upper surface of the body member forwardly of the bottom recess 47.

Means for quickly connecting and disconnecting a cannula having a mounting sleeve 26 to the handle means is best illustrated in FIGS. 4, 5 and 6. It has been noted that the mounting sleeve 26 is provided with a transverse cut out 34 intermediate its ends. In the forward portion of the handle means, a downwardly opening transverse recess 50 is provided in transverse alignment with an upwardly opening top recess 54, the recesses 50, 54 being connected by a port 55. Within bottom opening recess 50 is upwardly inserted a retaining ring 64 having an upwardly directed stem 65 which extends into and above the upper recess 54. The retaining ring 64 has a central opening 67 for reception of mounting sleeve 26 of cannula 16, the tapered configuration of the mounting sleeve serving to position the cut out 34 in the mounting sleeve in transverse alignment with retaining ring 64 whose central opening 67 receives mounting sleeve 26.

The retaining ring 64 is biased into upwardly directed locked position with the mounting sleeve 26 by means of a coil spring 62 around stem 65 and received within top recess 54. A pressure cap 66 of inverted cup shape covers the top of the stem 65 and the upper end of the coil spring 62 and may be secured to the stem by means of a screw 68. In normal locked position the bottom edges of the cup shaped cap 66 are spaced from the bottom of recess 54. When the cap is depressed by applying downward thumb pressure to cap 66, the retaining ring 64 is moved downwardly to disengage the bottom portion 69 of the retaining ring from the cut out 34 in the mounting sleeve and to thereby permit axial withdrawal of the mounting sleeve and attached cannula 16 from the handle means.

A replacement cannula having a similarly shaped mounting sleeve may be readily inserted into the front end of the handle means and pushed inwardly until its bottom cut out 34 is in transverse alignment with the retaining ring. Retaining ring 64 must be depressed in order to receive the mounting sleeve in control of central opening 67. Upon release of the force depressing the retaining ring, the retaining ring will spring upwardly to engage bottom portion 69 with cutout 34 and into locked position. In such locked position, it will be readily apparent that the cannula openings are in selected aligned relation with the handle means by reception of the pin 27 into the recess 44 of the handle means.

Means for controlling and regulating the suction force acting in the through bore 46 of the handle means and the passageway 18 of the cannula is provided by a plurality of openings 72 leading from the surface of the thumb recess 49 to the through bore 46 as shown in FIG. 2. The size or inner diameter of each opening 72 is relatively small so that suction forces acting on the surface area of a surgeon's glove covering one of the openings is relatively small and displacement of the glove material into the small opening by reason of the suction force is minimized. Thus, tearing of the surgeon's glove material which exercising control over the vacuum forces by moving the surgeon's thumb into covering and uncovering position of the openings in the bottom of the thumb recess is virtually eliminated. Further, since the surface of the thumb recess 49 is smooth and may be polished, the edges of the openings 72 at the surface of recess 49 may be slightly burnished and are restricted in their engagement with glove material so that tearing of the glove material is inhibited.

The plurality of small diameter openings 72 provide means for controlling the suction forces applied to the cannula distal end portion and also to the through bore 46. The aggregate flow area of the plurality of openings 72 may be approximately that of the flow area of the through bore 46. Under conditions of applying full suction force to the distal end of the cannula for removal of fatty tissue the thumb of the surgeon may fully cover all of the openings 72 in the thumb recess. Such suction force acting at the end of the cannula may be variably reduced by moving the thumb relative to the plurality of openings 72 so as to open one or more of the openings to atmospheric air pressure. Control of the suction force acting on the fatty tissue at the distal end of the cannula is thus provided by movement of the surgeons' thumb relative to the plurality of openings 72.

Under conditions where the through bore 46 and the fatty tissue conducting tube 14 become clogged by fatty tissue deposits, the openings 72 may be completely uncovered to allow the sucking of atmospheric air through the openings 72 into the through bore 46 to assist in clearing blockage of the fatty tissue conducting tube 14. Since the flow area of the openings 72 is substantially equivalent to the flow area of through bore 46, the effect of uncovering all of the opening 72 is essentially the same as removal of the cannula from the incision in order to permit clearance of blockages in the passageways conducting the fatty tissue. Such complete removal of the cannula from the incision to accomplish this purpose was one of the disadvantages of some of the prior art instruments.

Handle means 40 and tube means 14 may be provided with a swivel means 80 for interconnecting the handle means and tube means and to facilitate manipulation of the handle means and cannula 16 attached thereto during a lipectomy procedure.

Exemplary swivel means are best illustrated in FIGS. 10 and 11.

In FIG. 10, end portion 48 of handle means 40 is provided with a reduced diameter external male thread 49 which mates or threadedly engages with an internal female thread 82 of a swivel collar 86. Collar 86 in full threaded engagement is seated on a shoulder 87 of the handle means. Collar 86 also provides an end opening 89 of reduced diameter for reception therethrough of a swivel fitting 84 which may be inserted into and carried by tube means 14. Swivel fitting 84 includes an annular shoulder 88 which is received within an annular internal recess 90 provided in the swivel collar 86. Swivel fitting 84 also includes 0-ring seal means 92 which sealingly engages the fitting 84 and the internal surface of the end enlarged chamber 96 of the handle means. The swivel fitting 84 has a through passageway which communicates with the through passageway 46 of the handle means. Swivel fitting 84 may readily rotate about its longitudinal axis which coincides with the longitudinal axis of the handle means and thus permits the handle means to move rotationally with respect to the fatty tissue conducting tube 14.

The swivel means 80 provides relative movement of the handle means with respect to the tube 14 and thereby facilitates manual manipulation of the handle means through large degrees of movement of the handle means and cannula 16 by the surgeon during a lipectomy procedure.

The swivel means provides a connection to the handle means without leakage or reduction of vacuum and suction forces occurring in the passageway 46 of the handle means because of the sealing by the 0-ring means 92. It will be understood that the swivel fitting and the internal surfaces of the interior chamber 96 may be provided a close machined tolerance so that leakage between the swivel fitting, swivel collar, and handle means shoulder 87 may be reduced to an effective minimum.

An alternative embodiment of swivel means is illustrated by the swivel means 200 in FIG. 11. In this example, the construction of the swivel means is similar to that of FIG. 10 and the similar features of the swivel collar, swivel fitting and end portion of the handle means will not be referred to for brevity purposes. In this example, the tolerances between a swivel collar 208, the swivel fitting 209 and the handle end portion 210 may be subjected to spring biasing forces to facilitate relative rotational movement between the fitting 209 and the swivel collar 208. The end face of handle means 210 may be provided with a longitudinal recess 203 which receives a coil spring 202 having one end providing a seat for a ball bearing 204 which may bear against the end face of swivel collar 208. Swivel collar 208 in its threaded connection with the handle means is placed under a biasing force and may be finely adjusted so that the relative rotation between the swivel fitting 209 and the swivel collar at the annular rib or shoulder and annular recess respectively may be adjusted to facilitate relative rotational movement.

The examples of the swivel means described above provides relative rotational movement between the tube 14 and handle means. Other swivel means may be employed to provide additional relative movement by use of a universal swivel joint utilizing a ball and socket arrangement.

The advantages of the above-described apparatus and instrument means will be readily apparent to those skilled in the art. A selected cannula may be rapidly, quickly and easily connected to the handle means by depressing the pressure cap 66 to position the retaining ring with its opening in alignment with the passageway 46 so that the mounting sleeve of the selected cannula may be simply inserted lengthwise into the forward end of the handle means until its end face 35 abuts with an internal shoulder 37 provided in passageway 46. The tapered configuration of the mounting sleeve and its corresponding socket also positions the mounting sleeve and cannula in transverse alignment with the bottom portion 69 of the retaining ring. Upon release of pressure from the cap 66, the retaining ring bottom portion 69 will move transversely into locking engagement with the cutout 34 provided in the mounting sleeve. In this assembly operation, the pin 27 on the mounting sleeve is received in the recess 44 and the openings in the distal end of the cannula are oriented in proper relation with respect to the grasping of the handle means by the surgeon. Connection and disconnection of selected cannulas are quickly and readily accomplished so that a lipectomy procedure or operation is facilitated if the surgeon desires to employ a different type of cannula.

In the lipectomy procedure, the longitudinal opening 22 and the side openings 24 and 25 arranged diagonally transversely of the cannula provide effective openings for inflow of fatty tissue when the distal end portion of the cannula is moved in different directions and locations underneath the skin of the patient.

Control of the suction forces is readily achieved and maintained by relative movement of the thumb of the surgeon over the plurality of openings 72 provided in the handle as previously described. The plurality of openings are also so arranged that the chances of the material of a glove covering the thumb of the surgeon being caught on edges of the opening or torn by such opening are minimized.

It will be understood that various modifications and changes may be made in the apparatus and surgical means described above which may come within the spirit of this invention and all such changes and modifications coming within the scope of the appended claims are embraced thereby.

I claim:

1. An Apparatus for removing subcutaneous fatty tissue comprising in combination:

a suction source;

a surgical instrument means for removing fatty tissue;

a tube means for interconnecting said suction source and said instrument means for conducting tissue under aspirating conditions;

said instrument means including:

a cannula having a through passageway, one end of said cannula having a configures end closure portion provided with a side inlet opening to said passageway:

a mounting sleeve member fixed on the other end of said cannula;

a handle means having a through bore receiving at one end said mounting sleeve member for interconnecting said cannula and handle means, said handle means receiving at its other end said tube means for providing communication between said suction source and said cannula's configured end;

said cannula having an axis coaxial with said through bore;

said mounting sleeve member and said handle means having means for orienting said configured end of said cannula with said handle means;

a control means on said handle means for varying the suction forces in said cannula passageway;

said control means including a first concave recess in said handle means, and a plurality of spaced holes extending from said recessed to said through bore in said handle means;

a means for quickly connecting and disconnecting said handle means from said cannula;

a retaining means carried by said handle means for releasably engaging said mounting sleeve member on said cannula;

said retaining means having a spring bracing said retaining means into locked position; and said retaining means is located forwardly of said first recess on said handle means and including a cap to facilitate applying pressure to said retaining means;

a swivel means interconnecting said handle means and one end of said tube means whereby said handle means and said cannula maybe manipulated over a wide range of positions relative to said tube means during withdrawal of said fatty tissue under suction forces applied subcontaneously through a skin surface incision.

2. A surgical instrument comprising:

a handle means having a longitudinally extending bore;

a cannula having a passageway providing communication with said bore at one end, said passageway providing communication at its other end with an opening means adjacent to the end of the cannula;

said opening means including a forward longitudinally extending opening promixate to the adjacent end of said cannula;

said opening means also including an elongated opening having its longitudinal axis disposed transversely of the axis of said cannula and spaced rearwardly from said longitudinal opening;

said cannula having an end portion of convex configuration forwardly of the longitudinal opening to said passageway and a mounting sleeve member on the other end of said cannula;

an interconnecting means on the end of said handle means opposite to said cannula for interconnecting said handle means to a suction source for aspirating biological substances;

said interconnection means including a swivel means and a means for carrying biological substances;

said swivel means enabling manipulation of the handle means and cannula over a wide range of positions relative to said means for carrying biological substances;

a control means on said handle means for varying the suction forces in said cannula passageway;

said control means including:

a concave recess in said handle means having a smooth surface, and a plurality of spaced holes extending from said recess to said bore in said handle means;

a retaining means carried by said handle means and located forwardly of said recess for releasably engaging said mounting sleeve member on said cannula;

said retaining means further including a spring bracing said retaining means into a locked position, and a cap to facilitate applying pressure to said retaining means.

* * * * *